United States Patent [19]
Del Rossi et al.

[11] Patent Number: 5,245,101
[45] Date of Patent: Sep. 14, 1993

[54] ISOPARAFFIN:OLEFIN ALKYLATION PROCESS AND CATALYST COMPLEX

[76] Inventors: Kenneth J. Del Rossi, 8 La Tour Ct., Woodbury, N.J. 08096; Albin Huss, Jr., 51 Stirling Way, Chadds Ford, Pa. 19317; Samuel A. Tabak, 204 E. Pine St., Wenonah, N.J. 08090

[21] Appl. No.: 608,856

[22] Filed: Nov. 5, 1990

[51] Int. Cl.$^5$ .............................................. C07C 2/58
[52] U.S. Cl. .................................. 585/726; 585/721; 585/732
[58] Field of Search ..................... 502/203, 208; 568/2; 585/721, 726, 732

[56] References Cited

U.S. PATENT DOCUMENTS

| | | |
|---|---|---|
| 2,296,370 | 9/1942 | Slotterbeck . |
| 2,296,371 | 9/1942 | Slotterbeck . |
| 2,345,095 | 3/1944 | Bruner et al. . |
| 2,471,922 | 5/1946 | Axe ................................. 502/203 |
| 3,631,122 | 12/1971 | Berger . |
| 3,862,258 | 1/1975 | Huang et al. . |
| 3,873,634 | 3/1975 | Hoffman . |
| 3,925,500 | 12/1975 | Wentzheimer . |
| 4,384,161 | 5/1983 | Huang ............................... 585/722 |
| 4,795,728 | 1/1989 | Kocal ................................ 502/162 |
| 5,173,467 | 12/1992 | Del Rossi ........................... 585/726 |

FOREIGN PATENT DOCUMENTS 545441 8/1939 United Kingdom .
550711 8/1940 United Kingdom .

OTHER PUBLICATIONS

L. F. Albright et al., "Alkylation of Isobutane with $C_4$ Olefins", 27 Ind. Eng. Chem. Res., 381–397, (1988).
Handbook of Petroleum Refining Processes 23–28 (R. A. Meyers, ed., 1986).

*Primary Examiner*—Helen M. S. Sneed
*Assistant Examiner*—E. D. Irzinski

[57] ABSTRACT

The invention provides a catalyst complex for promoting alkylation of an isoparaffin with an olefin, said catalyst complex comprising the reaction product of $BF_3$ and at least one selected from the group consisting of $H_3PO_4$ and $H_2O$; and, additionally, excess $BF_3$ in concentration of from about 10 ppm (weight) to about 5 percent by weight of the total isoparaffin and olefin feed.

The invention further provides a process for the alkylation of an isoparaffin with an olefin by contacting a mixture of isoparaffin and olefin with the catalyst complex of the invention, decanting the hydrocarbon product from the catalyst complex, and deacidifying the hydrocarbon product.

11 Claims, 3 Drawing Sheets

ISOPARAFFIN:OLEFIN ALKYLATION PROCESS AND CATALYST COMPLEX

FIELD OF THE INVENTION

The present invention relates to a novel alkylation catalyst complex and to an alkylation process employing such catalyst complex.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

U.S. Pat. No. 4,795,728 to Kocal, for example, teaches a hydrofluoric acid catalyzed alkylation process for producing motor fuel. The hydrofluoric acid catalyst complex includes from 0.5 to 5 weight percent of a cationic or anionic surfactant component enabling the process to be operated at an olefin:acid volumetric feed ratio of greater than 1.0 while maintaining acceptable alkylate quality.

Both hydrofluoric and sulfuric acid catalysts are gradually depleted in continuous alkylation processes and must be regenerated or replenished by mixture with fresh acid to maintain acid strength, reaction rate, and the resulting alkylate quality. Specifically, alkylate quality responds directly to increasing acid strength, and the acid makeup or regeneration rate is typically controlled together with other process variables such as temperature and space velocity, to meet a required alkylate quality specification.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Catalyst complexes comprising $BF_3$ as well as $BF_3:H_3PO_4$ adducts have been proposed, and are discussed in greater detail below. While these catalysts effectively overcome the safety and environmental drawbacks of sulfuric and hydrofluoric acid alkylation systems, the volume and quality of $BF_3$ alkylates have not, in the past, proven comparable to that of sulfuric or hydrofluoric acid alkylates.

U.K. Patent 545,441, assigned to Standard Oil Development Company, teaches a $BF_3:H_3PO_4$ catalyzed isoparaffin-olefin alkylation process.

U.S. Pat. No. 2,345,095 to Bruner teaches a paraffin-olefin alkylation process catalyzed by a boron trifluoride-water complex, represented by the formula $BF_3:nH_2O$, where n is preferably from 1 to 1.5. The Bruner reference notes at page 2, left hand column, lines 13–23, that the $BF_3:H_2O$ catalyst complex behaves similarly to sulfuric acid but is a superior alkylation catalyst because $BF_3:H_2O$ does not promote oxidation to undesired byproducts.

U.S. Pat. Nos. 2,296,370 and 2,296,371 to Slotterbeck disclose a $BF_3:H_2O:HF$ catalyst system and an isoparaffin-olefin alkylation process employing the same. The catalyst system is said to avoid yield loss due to oxidation of the resulting alkylate product. The Slotterbeck '370 and '371 patents also discuss loss of catalytic activity due to diminishing acid strength; see the Slotterbeck '370 patent at page 2, right hand column at line 75 through page 3, left hand column at line 55, and the the Slotterbeck '371 patent at page 2, right hand column at line 66, through page 3, left hand column at line 41, U.K. Patent 550,711 teaches a process for increasing the activity of at least partially spent $BF_3:H_2O$ catalyst systems for reuse in an organic condensation reaction. Briefly, the process volatilizes $BF_3$ from the liquid catalyst mass to the extent required to promote separation of a distinct hydrocarbon phase from the catalyst mass. This hydrocarbon phase is then decanted off and fresh $BF_3$ is added to restore catalytic activity.

Canadian Patent 424,000 teaches a process for producing gasoline boiling range hydrocarbons from isobutane and a normally gaseous olefin by absorbing the olefin in phosphoric acid of at least 75 weight percent concentration with an amount of isobutane equal to at least three moles of isobutane per mole of alkyl phosphate in the presence of a catalytic mixture of phosphoric acid and boron halide at temperature between 20° C. and 60° C.

U.S. Pat. No. 3,873,634 to Hoffman teaches a method of increasing the rate of ethylene alkylation by isobutane by carrying out the reaction simultaneously with the alkylation of a small amount of a higher weight olefin in the presence of a $BF_3:H_3PO_4$ catalyst complex at low temperature and pressure.

U.S. Pat. No. 3,925,500 to Wentzheimer discloses a combined acid alkylation and thermal cracking process employing a $BF_3:H_3PO_4$ acid catalyst in which unconverted propane and ethane from the alkylation process are converted, for example, to propylene and ethylene which are subsequently alkylated with isobutane to evolve a valuable liquid fuel.

The problem of acid consumption remains as an obstacle to commercialization of Lewis acid catalyzed alkylation, first because of the high cost of suitable Lewis acids, and second because of the cost of disposing of an acid neutralization byproduct if the acid is not recycled. Specifically, it would be highly beneficial to avoiding the capital and operating costs associated with a Lewis acid/light aliphatic fractionation section. For example, in a typical $BF_3$-catalyzed isobutane:butene alkylation process employing feeds containing minor amounts of lighter hydrocarbons, the reactor effluent product is first fractionated to separate $C_4-$ components from $C_5+$ alkylate. The overhead stream from this fractionation step typically contains not only $BF_3$ but also unreacted propane which must be removed before the $BF_3$ is recycled to the alkylation reactor. While the two components are separable by distillation, their close boiling points require a tall, expensive distillation tower. Further, the tower must be protected from corrosive attack by $BF_3$, for example, by the use of nickel-rich alloys such as Monel.

Moreover, residual $BF_3$ carried over into the product fractionation section reacts to form nonvolatile boron hydrates which precipitate out and form insoluble deposits inside the distillation columns and their associated reboilers. U.S. Pat. No. 3,631,122 reports that these deposits cause an undesirable deterioration in distillation column performance, and discloses a process for reacting these hydrates and removing the reaction product from the system. But clearly, it would be even more beneficial to preventing carryover of $BF_3$ into the product fractionation section to avoid formation of these insoluble deposits.

U.S. Pat. No. 4,384,161 teaches a process of alkylating isoparaffins with olefins in the presence of a catalyst comprising a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms of zeolite Y, and a Lewis acid such as $BF_3$, $SbF_5$, or $AlCl_3$. The use of a large pore zeolite in combination with a Lewis acid is shown in the '161 patent to increase the activity and selectivity of the zeolite thereby effecting alkylation with high olefin space velocity and low isoparaffin:olefin ratio.

Allowed U.S. patent application Ser. No. 425,497, filed Oct. 17, 1989, which is a continuation of U.S. patent application Ser. No. 219,130, filed Jul. 15, 1988, now abandoned, discloses heterogeneous isoparaffin:olefin alkylation in the presence of a large-pore zeolite, a Lewis acid, and water. The Lewis acid is suitably present in an amount which exceeds that required to saturate zeolite as well as any binder or matrix material which may be present.

Alkylate gasolines, such as those produced by the processes discussed above, are rich in isoparaffins and contain essentially no sulfur and aromatics. Generally exhibiting strong sensitivity to octane-enhancing additives, alkylate gasolines are prime candidates for blending into motor gasolines to meet the increasingly stringent environmental regulations restricting gasoline vapor pressure and aromatics content. However, none of these alkylate gasolines is suitable for use as blending stocks unless they are free from the acid components of the alkylation catalyst. Specifically, the Lewis acid component of the alkylation catalyst complexes employed in the processes discussed above must be removed before the alkylate product can be blended into gasoline.

Once-through $BF_3$ operation together with product deacidification, if it had been previously contemplated, would have been eliminated from serious consideration due to prohibitive costs both the makeup Lewis acid as well as for disposal of the neutralization byproduct. Separating the Lewis acid and recycling the purified acid, on the other hand, reduces acid consumption but requires a substantial capital investment for fractionation process equipment, as noted above. Thus it would be desirable to provide a Lewis acid catalyzed alkylation process which achieves the alkylate quality of previously known but less environmentally acceptable processes while at the same time producing an alkylate product stream containing sufficiently low levels of Lewis acid that the product stream could be ecomonically deacidified, thereby affording once-through $BF_3$ operation while avoiding the expense associated with Lewis acid recovery and recycle.

SUMMARY OF THE INVENTION

In accordance with the present invention, it has been found that one particular Lewis acid, $BF_3$, reacts with certain liquids to form alkylation catalyst complexes which effectively catalyze isoparaffin:olefin alkylation at extremely low levels of excess $BF_3$. The product resulting from isoparaffin:olefin alkylation in the presence of these catalyst complexes contains $BF_3$ in sufficiently dilute concentrations that neutralization is a feasible, and indeed, economically attractive, alternative. As used herein, the term "catalyst complex" refers to the reaction product of a specified liquid with $BF_3$, but is not presented to limit the scope of the invention by recitation or suggestion of a theoretical chemical structure for the catalytically active reaction product. Further, the the singular forms "catalyst complex" and "reaction product" are defined as including the plural forms "catalyst complexes" and "reaction products"; similarly, the plural forms are defined to include the singular.

The present invention includes both an isoparaffin:olefin alkylation catalyst complex and an isoparaffin:olefin alkylation process. In contrast to previously known alkylation catalysts and processes, which suggest that more concentrated acid catalysts maximize yield of isoparaffins and suppress undesirable olefin oligomerization side reactions, it has surprisingly been found that relatively low concentrations of excess $BF_3$ in the presence of the reaction product of $BF_3$ with $H_3PO_4$, $H_2O$, or both $H_3PO_4$ and $H_2O$, improve alkylate quality. These results are of particular importance in the preferred embodiments of the process of the invention, which alkylates butene with isobutane to form isoparaffin-rich alkylate gasoline. The process not only improves alkylate octane and yield, but also decreases production costs by eliminating the need for costly separation and recycle of $BF_3$. Specifically, the present invention enables the refiner to operate an $BF_3$-catalyzed isoparaffin:olefin alkylation process at $BF_3$ injection rates such that the concentration of $BF_3$ in the resulting alkylate product stream warrants removal but not recovery and recycle. Examples of suitable deacidification steps include neutralizaiton, complexation, or sorption.

The invention thus provides in a first embodiment, a catalyst complex for promoting alkylation of an isoparaffin with an olefin, said first catalyst complex comprising the reaction product of $BF_3$ and $H_3PO_4$ in molar ratios of from about 0.5:1 to about 1.5:1, and, additionally, excess $BF_3$ in concentration of from about 10 ppm (weight) to about 5 percent (weight) based on the total isoparaffin:olefin feed.

The invention further provides in a second embodiment, a catalyst complex for promoting alkylation of an isoparaffin with an olefin, said catalyst complex comprising the reaction product of $BF_3$ and $H_2O$ in molar ratios of from about 0.5:1 to about 1.5:1, and, additionally, about 10 ppm (weight) to about 5.0 percent (weight) excess BF$_3$ based on the total isoparaffin:olefin feed.

In a third embodiment of the catalyst complex of the invention, the invention provides an isoparaffin:olefin alkylation catalyst comprising the reaction product of BF$_3$, H$_3$PO$_4$, and H$_2$O and, additionally, excess BF$_3$ of from about 10 ppm (weight) to about 5.0 percent (weight) based on the total isoparaffin:olefin feed.

The invention further provides, in a first process aspect, a continuous process for the alkylation of an isoparaffin with an olefin comprising the steps of:

(a) contacting H$_3$PO$_4$ with BF$_3$ in molar ratios of from about 0.5:1 to about 1.5:1 to evolve an isoparaffin:olefin alkylation catalyst complex and, additionally, excess BF$_3$ in concentrations of from about 10 ppm (weight) to about 5.0 percent (weight) excess BF$_3$ based on the total isoparaffin:olefin feed;

(b) reacting an isoparaffin containing from 4 to 20 carbon atoms with an olefin containing from 2 to 12 carbon atoms in an alkylation reaction zone in the presence of said catalyst complex of step (a) under conversion conditions including temperature of from about $-40°$ C. to about 200° C., pressure in the range of subatmospheric to about 5000 psig, and weight hourly space velocity from 0.01 to 100 hr.$^{-1}$ based on total olefin feed;

(c) withdrawing a product stream containing gasoline boiling range hydrocarbons and catalyst complex from said alkylation reaction zone of step (b) and recycling at least a portion of said catalyst complex to said alkylation reaction zone.

The invention further provides, in a second process aspect, a continuous process for the alkylation of an isoparaffin with an olefin comprising the steps of:

(a) contacting H$_2$O and BF$_3$ in molar ratios of from about 0.5:1 to about 1.5:1 to evolve a catalyst complex and, additionally, from about 10 ppm (weight) to about 5.0 percent (weight) excess BF$_3$ based on the total isoparaffin:olefin feed;

(b) reacting an isoparaffin containing from 4 to 20 carbon atoms with an olefin containing from 2 to 12 carbon atoms in an alkylation reaction zone in the presence of said catalyst complex of step (a) under conversion conditions including temperature of from about $-40°$ C. to about 200° C., pressure in the range of subatmospheric to about 5000 psig, and weight hourly space velocity from 0.01 to 100 hr.$^{-1}$ based on total olefin feed; and (c) withdrawing a product stream containing gasoline boiling range hydrocarbons and catalyst complex from said alkylation reaction zone of step (b) and recycling at least a portion of said catalyst complex to said alkylation reaction zone.

The invention still further provides, in a third process aspect, a continuous process for the alkylation of an isoparaffin with an olefin comprising the steps of:

(a) contacting H$_2$O, H$_3$PO$_4$, and BF$_3$ in molar ratios sufficient to evolve an isoparaffin:olefin alkylation catalyst complex, and, additionally, excess BF$_3$ in concentrations of from about 10 ppm (weight) to about 5.0 percent (weight) excess BF$_3$ based on the total isoparaffin:olefin feed;

(b) reacting an isoparaffin containing from 4 to 20 carbon atoms with an olefin containing from 2 to 12 carbon atoms in an alkylation reaction zone in the presence of said catalyst complex of step (a) under conversion conditions including temperature of from about $-40°$ C. to about 200° C., pressure in the range of subatmospheric to about 5000 psig, and weight hourly space velocity from 0.01 to 100 hr.$^{-1}$ based on total olefin feed;

(c) withdrawing a product stream containing gasoline boiling range hydrocarbons and catalyst complex from said alkylation reaction zone of step (b) and recycling at least a portion of said catalyst complex to said alkylation reaction zone.

In preferred process embodiments, the isoparaffin is isobutane the olefin is butene, the alkylated product is separated from the catalyst complex by decantation, and the hydrocarbon phase including the alkylated product withdrawn from an upper decanted layer is deacidified to remove residual BF$_3$. Suitable deacidification steps include neutralizaiton, complexation, or sorption.

DETAILED DESCRIPTION

The present invention includes both an isoparaffin:olefin alkylation catalyst and an alkylation process which provides improved alkylate quality at low levels of excess BF$_3$ and eliminates capital and operating costs associated with BF$_3$ recovery and recycle.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The most preferred olefins include the C$_3$ and C$_4$ olefins, for example, propylene, butene-1, butene-2, isobutylene, or a mixture of one or more of these olefins. Suitable feedstocks for the process of the present invention are described in U.S. Pat. No. 3,862,258 to Huang et al. at column 3, lines 44-56, the disclosure of which is incorporated by reference as if set forth at length herein.

The overall molar ratio of isoparaffin to olefin in the reactor feed during normal alkylation operation is generally between 1:1 and 100:1, preferably between about 5:1 and about 20:1.

Process Conditions

The present alkylation process is suitably conducted at temperatures of from about −40° C. to about 500° C., preferably from below about 40° C. to avoid undesirable side reactions, and most preferably from about 0° C. to about 20° C. Lower reaction temperatures are preferred to maximize alkylate octane.

Operating pressure is controlled to maintain the reactants in the liquid phase, and is suitably from about 50 to about 5000 psig, preferably from about 50 to about 1500 psig, and more preferably from about 80 to about 200 psig. Weight hourly space velocity ranges from about 0.01 to about 100 based on total olefin feed to the reaction zone. The most preferred weight hourly space velocity varies within this range as a function of reaction temperature and feedstock composition. Weight hourly space velocity is readily optimized to attain a desired octane specification with only minimum trial and error.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

The process can be carried out in any suitable vessel, for example, in a continuous stirred tank reactor such as that typically employed in sulfuric acid alkylation or in a tubular riser type reactor such as is typically used for hydrofluoric acid alkylation.

Catalyst Complex

A first embodiment of the catalyst complex of the present invention comprises the reaction product of $BF_3$ and $H_3PO_4$ in molar ratios of $BF_3:H_3PO_4$ of from about 0.5:1 to about 1.5:1, and, additionally, excess $BF_3$ from about 10 ppm (weight) to about 5 percent (weight) based on the total isoparaffin:olefin feed, preferably from about 25 ppm (weight) to about 2.5 percent (weight) excess $BF_3$, and more preferably from about 50 ppm (weight) to about 1 percent (weight) excess $BF_3$. Effective overall concentrations of the $BF_3:H_3PO_4$ reaction product and excess $BF_3$ constituents of the catalyst complex will therefore vary slightly as varying process conditions such as temperature and pressure affect the solubility of $BF_3$ in the $H_3PO_4$, but these concentrations will generally fall within the range of from about 30 to about 65 weight percent $BF_3$, from about 20 to about 60 weight percent $H_3PO_4$.

A second embodiment of the catalyst complex of the present invention comprises the reaction product of $BF_3$ and $H_2O$ in molar ratios of from about 0.5:1 to about 1.5:1, and, additionally, excess $BF_3$ in concentrations of from about 10 ppm (weight) to about 5.0 percent (weight) based on the total isoparaffin:olefin feed.

The reaction products of $BF_3$, $H_3PO_4$, and $H_2O$ are effective alkylation catalysts in admixture. Thus a third embodiment of the catalyst complex of the invention comprises the reaction products of $BF_3$, $H_3PO_4$, and $H_2O$, and, additionally, excess $BF_3$ of from about 10 ppm (weight) to about 5.0 percent (weight) based on the total isoparaffin:olefin feed.

Alkylation Process

The process of the present invention is most preferably operated in a continuous mode. In the preferred continuous process embodiment, $BF_3$ addition rates to the alkylation reaction zone are controlled at rates of from about 10 ppm (weight) to about 5 percent (weight) $BF_3$, and typically fall within the range of from about 25 ppm (weight) to about 1 percent (weight) of the total isoparaffin:olefin feed to the alkylation reaction zone.

Figure 1:
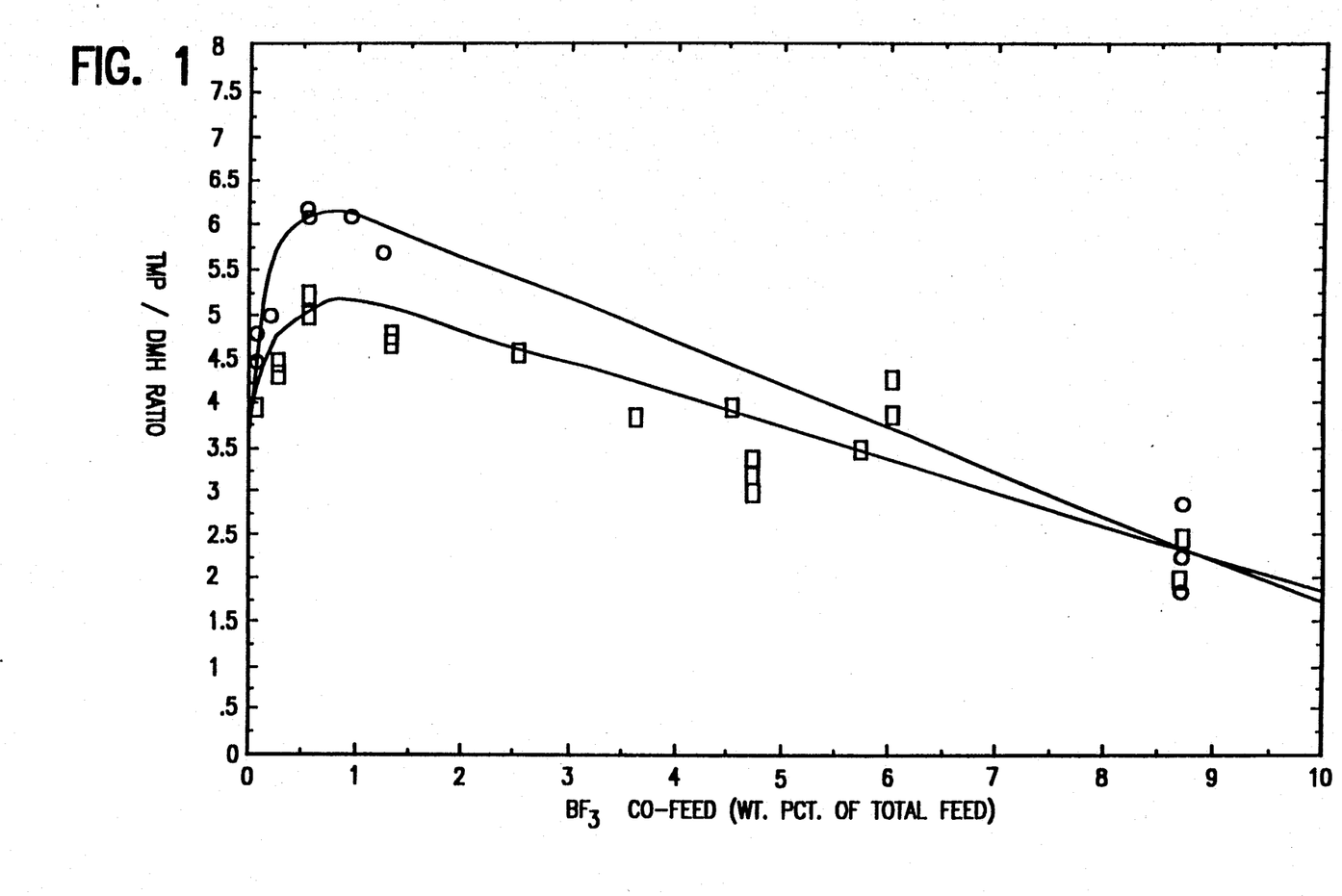
FIG. 1 illustrates the effect of BF$_3$ co-feed level on the distribution of C$_8$ paraffins in the alkylate product stream from the alkylation of 2-butene with isobutane in the presence of a BF$_3$:H$_3$PO$_4$:H$_2$O catalyst at weight hourly space velocities ranging from 0.25 to 1.3 hr$^{-1}$. Data collected from experimental runs with a 5:1 isoparaffin:olefin ratio are shown by rectangular data points while the circular data points show results from experimental runs with a 10:1 isoparaffin:olefin ratio. The y-axis represents alkylate quality by the weight ratio of trimethylpentane to dimethylhexane, hereinafter referred to as the TMP/DMH ratio. The x-axis represents BF$_3$ cofeed rate as a weight percentage of the total isoparaffin:olefin feed to the reaction zone.

FIG. 1 illustrates the effect of $BF_3$ co-feed level on the distribution of $C_8$ paraffins in the alkylate product stream from the alkylation of 2-butene with isobutane in the presence of an alkylation catalyst comprising a $BF_3:H_3PO_4:H_2O$ reaction product at weight hourly space velocities ranging from 0.25 to 1.3 $hr^{-1}$. Data collected using a 5:1 isoparaffin:olefin ratio are shown by rectangular data points while the circular data points show results for a 10:1 isoparaffin:olefin ratio. The y-axis represents alkylate quality by the weight ratio of trimethylpentane to dimethylhexane, hereinafter referred to as the TMP/DMH ratio. Octane rating has been found to be a direct function of the relative balance between trimethylpentane and dimethylhexane in the alkylate product, with larger numerical TMP/DMH ratios associated with higher octane ratings. The x-axis represents the rate of $BF_3$ co-feed in weight percent of the total feed. FIG. 1 shows the most preferred $BF_3$ dosage for $BF_3:H_3PO_4$ catalyzed isoparaffin:olefin alkylation is in the range of about 250 ppm (weight) to about 2% (weight) based on the total isoparaffin:olefin feed to the reaction zone for the experimental process conditions and catalyst composition as described above. The optimum $BF_3$ level for a particular set of process conditions varies within the range of from about 10 ppm (weight) to about 5% (weight), based on the total isoparaffin:olefin feed to the reaction zone.

Product Deacidification

By removing residual acid in the alkylation reactor product stream before it reaches the product fractionation section, the present process avoids costly corrosion control measures otherwise required for recovery of acid-containing product. The hydrocarbon product effluent from the deacidification step must be essentially free of both residual Lewis acid as well as alkaline wash solution. More specifically, the hydrocarbon product effluent should contain no more than 10 ppm (weight) residual $BF_3$, and preferably contains less than 5 ppm (weight) of residual $BF_3$, based on the total hydrocarbon effluent from the reaction zone. Suitable deacidification process steps include one or more of sorption, neutralizaiton, or complexation.

Sorbents suitable for use in the present process must preferentially sorb Lewis acids from hydrocarbon gas streams having such compounds dissolved therein, and retain the sorbed Lewis acid until the enriched sorbent is contacted with a lean stripping fluid. Examples of such sorbents include both solid and liquid Lewis bases. Suitable Lewis bases which are normally solid under sorption conditions include calcium fluoride ($CaF_2$), as well as polyvinyl alcohol (PVA). Suitable Lewis bases which are normally liquid under sorption conditions include diethylether, dioxane and anisole.

Solid sorbents are preferably packed into fixed beds equipped with flow distributors to promote uniform contact with the solid sorbent. Lewis acid sorption by a liquid sorbent, on the other hand, may be carried out using various gas-liquid contacting means well known to those skilled in the art, for example, a tower containing trays or packing to improve liquid-vapor contact. The enriched sorbent is then stripped of Lewis acid by gas-liquid stripping of the sorbent liquid with an isoparaffin-containing alkylation feedstream. For a general survey of suitable vapor-liquid contacting techniques and process equipment, see A. L. Kohl, "Absorption and Stripping", HANDBOOK OF SEPARATION TECHNOLOGY, 340 (1987).

The residual acid may also be removed from the hydrocarbon product effluent stream via neutralization via contact with a base such as KOH or NaOH. A suitable apparatus for conducting this process step is a packed bed defluorinator containing substantially inert $Al_2O_3$ beads, as is commonly used to treat the depropanizer overhead stream in many commercial HF alkylation process units.

Process Flow

The reactor configuration for the process of the present invention is not critical; the process may be carried out in any suitable vessel, for example, a riser reactor or a stirred tank reactor. The liquid mixture from the stirred tank reactor is piped to a liquid-liquid separator, for example, a decanter, where the more dense liquid alkylation catalyst rapidly migrates to the bottom of the settler, while the gasoline-containing product floats to the top of the settler. The liquid catalyst is withdrawn from the bottom of the settler, and may be disposed and/or combined with fresh catalyst and sent back to the reactor. The hydrocarbon product is collected from the top of the settler and piped to a deacidification step, for example, a caustic scrubber where the hydrocarbon product contacts an aqueous caustic solution (NaOH) to remove residual acid.

Figure 2:
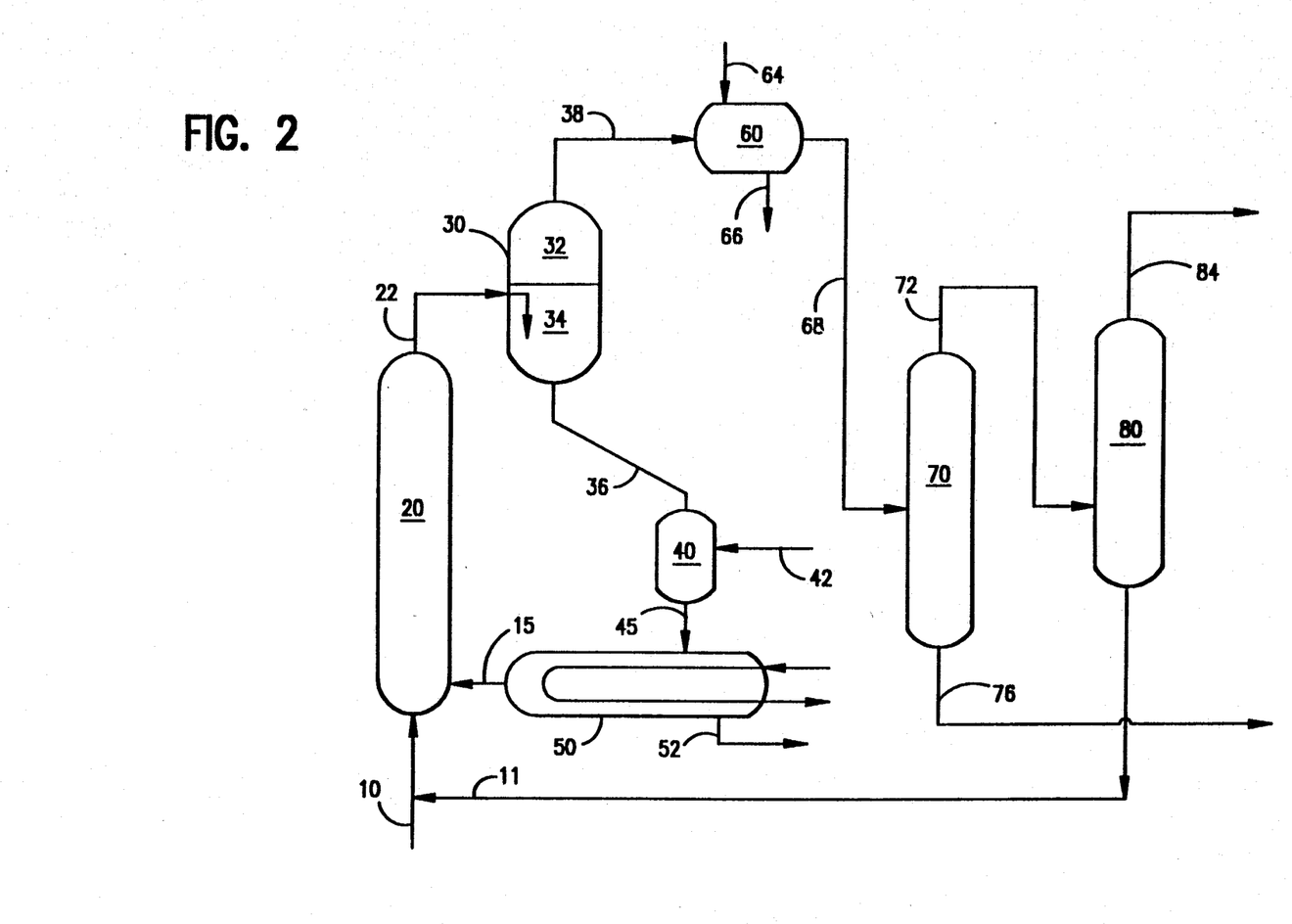
FIG. 2 schematically illustrates the major processing steps of a first embodiment of the process of the present invention in which an olefin is alkylated with an isoparaffin in the presence of a catalyst complex comprising the reaction product of BF$_3$ and H$_3$PO$_4$, and, additionally, excess BF$_3$, in a riser reaction zone.

Referring now to FIG. 2, a first embodiment of the process of the present invention is schematically illustrated. Feedstock containing isoparaffin and olefin flows through line 10 and is mixed with recycled isoparaffin from line 11 to provide a weight ratio of about 10:1 isoparaffin:olefin in the total feed to alkylation reactor 20. The isoparaffin is most preferably isobutane and the olefin is most preferably 2-butene. In the first embodiment of the invention as described herein, alkylation reactor 20 is a riser reactor as is commonly used in hydrofluoric acid alkylation processes. See, for example, 1 *Handbook of Petroleum Refining Processes* 23-28 (R. A. Meyers, ed., 1986), cited above, which is incorporated by reference as if set forth at length herein, for a general description of alkylation in a riser reactor.

A product stream containing partially spent catalyst complex, alkylated conversion products, and unreacted isoparaffin is withdrawn from alkylation reactor 20 through line 22 and charged to settler 30, preferably below the level of the heavier catalyst complex layer 34. The mixture readily separates due to the relative densities of the hydrocarbons and the $BF_3:H_3PO_4$ alkylation catalyst complex, which are approximately 0.6 g/cc and 1.6 g/cc, respectively.

The heavier catalyst complex accumulated in the lower section of 34 of settler 30, is withdrawn through line 36 and flows to mixing vessel 40 where the catalyst is admixed with fresh $BF_3$, or a mixture of $BF_3$ and $H_3PO_4$, which is added via line 42. The $BF_3$ charge rate to mixing vessel 40 is preferably controlled to restore the catalytic activity of the $BF_3:H_3PO_4$ complex with little or no excess $BF_3$. Thus typical excess $BF_3$ levels fall within the range of about 10 ppm (weight) to about 5 percent (weight) $BF_3$ based on the total isoparaffin:olefin feed to the reactor.

The catalyst then flows to catalyst cooler 50 through line 45 before being returned to reactor 20. The alkylation reaction is typically exothermic, and for this reason, the catalyst complex is precooled before it is returned to the reaction zone to maintain the alkylation reaction temperature within the preferred range. As noted above, temperature control in the alkylation reaction zone effects alkylate quality and is therefore an essential process control consideration. A suitable cooling medium withdraws heat from the catalyst complex, preferably by indirectly contacting the catalyst complex as the cooling medium flows through tubes of a shell-and-tube heat exchanger as illustrated. Any suitable cooling medium known to those skilled in the art may be employed, for example, chilled water or a solution of ethylene glycol in water.

Because the activity of the catalyst complex gradually diminishes over time, a portion of the catalyst complex is continuously or intermittently withdrawn from catalyst cooler 50 through line 52 for treatment in a regeneration facility or disposal in suitable facilities (not shown).

Turning now to processing the alkylated hydrocarbon products, the lighter hydrocarbon phase contained in the alkylation reactor effluent is charged to separator 30 and readily forms a discrete hydrocarbon phase in the upper section 32 of the separator. This hydrocarbon phase including not only alkylated product but also unreacted isobutane as well as small amounts of $BF_3$, is withdrawn from separator 30 and charged to a deacidification vessel 60, through line 38, which typically comprises a caustic (aqueous NaOH) wash. Fresh caustic enters the deacidification vessel 60 through line 64 and contacts the $BF_3$-containing hydrocarbon mixture. Because the hydrocarbon phase and the aqueous caustic phase are substantially immiscible, the two liquids are readily separated, with spent caustic and treated hydrocarbon being withdrawn from deacidification vessel 60 via lines 66 and 68, respectively. The minor amount of $BF_3$ contained in the hydrocarbon phase fed to the deacidification zone typically forms precipitate which is withdrawn with the spent caustic phase through line 66.

The deacidified hydrocarbon phase containing unreacted isobutane and lighter $C_4-$ aliphatics together with alkylated product flows to deisobutanizer separator 70 which separates the hydrocarbon stream into an overhead stream containing isobutane and lighter hydrocarbons and a bottom stream containing normal butane and gasoline boiling range alkylated product. The bottom stream is withdrawn from deisobutanizer 70 through line 76 for further fractionation (not shown) to reduce the alkylate gasoline vapor pressure or may be sent directly to product storage facilities (not shown). The overhead stream flows through line 72 to depropanizer 80 which splits off propane as an overhead stream through line 84 for resale or for use as fuel gas and recycles isobutane to line 10 through line 11 as described above. The deisobutanizer and depropanizer separators may comprise any suitable separation means known to those skilled in the art, for example, conventional multiple tray fractionation towers with reboilers and overhead condensers.

Figure 3:
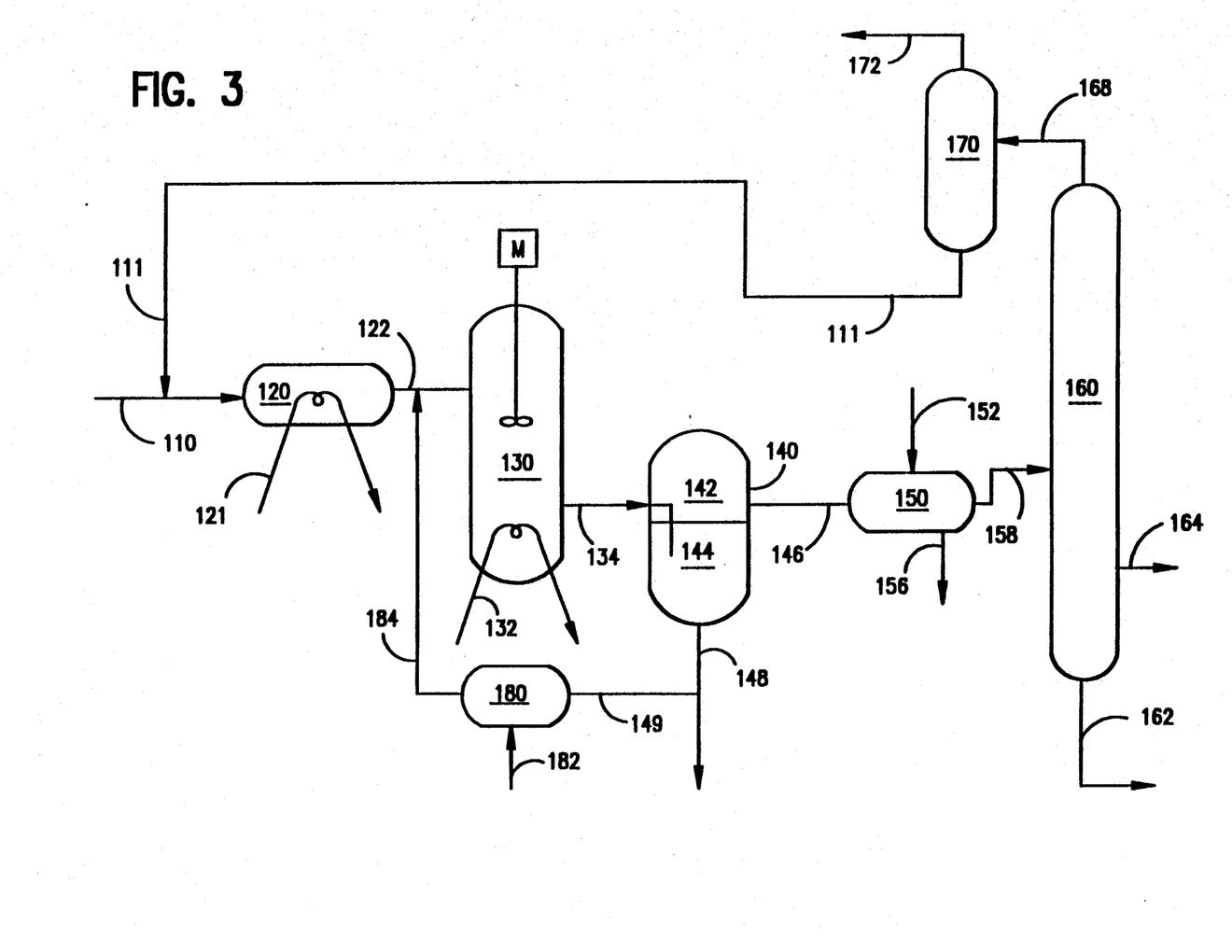
FIG. 3 schematically illustrates the major processing steps of a second embodiment of the process of the present invention in which an olefin is alkylated with an isoparaffin in the presence of a catalyst complex comprising the reaction product of BF$_3$ and H$_3$PO$_4$, and, additionally, excess BF$_3$, in a stirred tank reactor.

Referring now to FIG. 3, another embodiment of the process of the present invention is schematically illustrated in which the isoparaffin:olefin feedstock contacts the catalyst complex in a well stirred tank. A mixture of isoparaffin and olefin flows through line 110 and is mixed with recycled isoparaffin from line 111 to provide a weight ratio of about 10:1 isoparaffin:olefin in the total feed. The isoparaffin is most preferably isobutane and the olefin is most preferably 2-butene.

The mixed feedstream flowing through line 110 enters charge cooler 120 where it is cooled to a temperature slightly below the most preferred alkylation temperature as described above. The exothermic alkylation reaction then raises the temperature of the reactants to the preferred range as the conversion reaction progresses. As described above in the description of the first embodiment, the cooling medium preferably flows through the tubes 121 of a shell-and-tube heat exchanger. The cooling medium may comprise water with optionally added freezing point depressants such as ethylene glycol if alkylation process conditions require precooling the mixed feed to temperatures near the lower extremes of the preferred alylation temperature ranges, e.g. 0° C.

The cooled mixed feed is then withdrawn from charge cooler 120 through line 122, mixes with catalyst from line 184, and enters stirred tank reactor 130. Catalyst loading in stirred tank reactor 130 ranges from about 0.1 to about 75 volume percent catalyst complex, preferably from about 5 to about 25 volume percent catalyst complex.

If the exothermic heat load in reactor 130 so requires, a reactor cooling coil 132 may be positioned within the reactor to maintain temperature within the preferred range to assure consistent alkylate quality. Because the coolant temperatures required in the tubes 121 of cooler 120 and the reactor cooling coil 132 are approximately equivalent, the two heat exchangers may be supplied in parallel from a central cooler or chiller. As used herein, the term "cooler" refers to any suitable source of process cooling water, for example an underground well, a natural draft cooling tower, a forced air cooling tower, or a refrigeration unit. The term "chiller" as used herein refers more specifically to refrigeration units, particularly those refrigeration units which supply a chilled solution of water and a freezing point depressant such as ethylene glycol.

Generally, cooling towers are suitable for use in conjunction with the present process to supply water at temperatures as low as about 24° C. (75° F.) under cool to moderate atmospheric conditions. Reaction temperatures as low as about 10° C. (50° F.) may be achieved via autorefrigeration, i.e., flashing i-$C_4$ for cooling. For process temperatures below about 10° C. (50° F.), refrigeration units are typically employed to circulate a chilled aqueous mixture containing a freezing point depressant, for example, ethylene glycol.

The emulsion of unreacted isobutane, other light hydrocarbons, alkylation reaction products, and catalyst complex is withdrawn from stirred tank reactor 130 via line 134 and enters separator 140, preferably below the level of accumulated catalyst complex 144. The hydrocarbon phase, including not only alkylated product but also unreacted isobutane as well as small amounts of $BF_3$ readily accumulates in the upper section 142 of the separator and is withdrawn from separator 140 via overhead line 146. The hydrocarbon phase is charged to a deacidification vessel 150, where the hydrocarbon phase is treated to remove residual acid, typically with a caustic (aqueous NaOH) wash entering vessel 150 through line 152. This deacidification step proceeds generally as described above with reference to the first embodiment. The hydrocarbon phase and the aqueous caustic phase are readily separated, with spent caustic and treated hydrocarbon being withdrawn from neutralization vessel 150 via lines 156 and 158, respectively.

The heavier acid catalyst complex phase 144 is withdrawn from separator 140 through line 148 and flows to mixing vessel 180 through line 149 where the catalyst is admixed with fresh $BF_3$, or a mixture of $BF_3$ and $H_3PO_4$, which is added via line 182. The $BF_3$ charge rate to mixing vessel 180 is preferably controlled to restore the catalytic activity of the $BF_3$: $H_3PO_4$ complex with low levels of excess $BF_3$. Typical excess $BF_3$ levels range from about 10 ppm (weight) to about 5 percent (weight) $BF_3$ based on the total isoparaffin:olefin feed to the reactor.

The treated hydrocarbon phase then enters separator 160 where it is fractionated into a bottom alkylate-rich stream, a normal-butane rich side draw, and an isobutane-rich overhead stream, flowing through lines 162, 164, and 168, respectively. The bottom alkylate-rich stream contains isoparaffinic gasoline-boiling range hydrocarbons and is routed to storage or to gasoline blending facilities (not shown). The normal butane side draw may be resold or further upgraded elsewhere in the refinery complex (not shown). The overhead stream containing isobutane and lighter hydrocarbons flows through line 168 to depropanizer 170 where propane and lighter hydrocarbons are split off overhead through line 172 and routed to fuel gas or for further upgrading. The depropanized isobutane stream from the bottom of depropanizer 170 is then recycled to line 110 via line 111 where it enters the charge cooler 120 and is recycled through the alkylation process.

EXAMPLES

The following examples illustrate the range of excess $BF_3$ levels which maximize alkylate octane in accordance with the invention.

40 grams of orthophosphoric acid (85 weight % $H_3PO_4$; 15 weight % $H_2O$; purchased from Baker Chemical Company) were loaded into a 300 cc autoclave reactor. The reactor was filled with isobutane, cooled to 50° F., pressurized to 150 psig while stirring at 1000 rpm and the reactor contents were then saturated with $BF_3$ overnight at a rate of 25 cc $BF_3$ per minute. A mixed feed of isobutane and 2-butene was introduced at a rate of 0.4 $hr^{-1}$ weight hourly space velocity (WHSV) of olefin based on the $H_3PO_4$ component of the catalyst complex, and the $BF_3$ co-feed rate was reduced to an equivalent of 0.5 percent (weight) of the total hydrocarbon feed. These conditions were maintained for the first 11 days while catalyst performance was monitored. Following this period, $BF_3$ co-feed was terminated and the run was continued another 7 days to follow the performance of this catalyst in the absence of $BF_3$ addition.

Throughout the run, liquid product was withdrawn from an upper section of the autoclave reactor and collected in a receiver chilled to 0° C. (32° F.). The hydrocarbon product phase and the catalyst complex phase were found to separate readily within the reactor by decantation. The hydrocarbon liquid product withdrawn from the autoclave reactor found to be relatively free from catalyst complex, and loss of catalyst complex to the hydrocarbon product stream during the run was only minor. This was surprising in light of the fact that the autoclave reactor contained a stirrer as noted above, yield increased from 5.3 to 11.0 weight %, and the octane dropped from over 95.5 to around 94.0 (R+M)/2), the unexpected improvement in performance was demonstrated at extremely low $BF_3$ concentrations. Tables 2 and 3 show the results of additional experimental runs illustrating alkylate yield and quality as a function of excess $BF_3$ levels.

TABLE 1

(Liquid $BF_3:H_3PO_4:H_2O$ Catalyst)
(10/1 $IC_4/2$-$C_4$ = Feed, 50° F., 150 psig, 1000 RPM)

|  | Ex. 1 | Ex. 2 | Ex. 3 | Ex. 4 | Ex. 5 | Ex. 6 | Ex. 7 |
|---|---|---|---|---|---|---|---|
| Hrs. on Stream | 248 | 296 | 320 | 343 | 367 | 391 | 415 |
| WHSV Based on Olefin, $hr^{-1}$ | 0.36 | 0.37 | 0.37 | 0.37 | 0.37 | 0.37 | 0.37 |
| $BF_3$ Rate, wt. % of feed | 0.52 | 0.0 | 0.0 | 0.0 | 0.0 | 0.0 | 0.0 |
| Olefin Conversion, % | 100.0 | 99.8 | 99.8 | 97.5 | 97.1 | 97.2 | 97.0 |
| Yield (Grams $C_5+$ Product/ Grams Olefin Converted) | 1.98 | 1.95 | 2.00 | 1.92 | 1.96 | 1.99 | 1.91 |
| Product Distribution in $C_5+$, wt. % |  |  |  |  |  |  |  |
| $C_5$-$C_7$ | 9.3 | 8.7 | 10.2 | 11.8 | 13.7 | 14.4 | 15.5 |
| $C_8$'s | 86.2 | 86.0 | 82.8 | 80.1 | 77.3 | 75.5 | 73.5 |
| $C_9+$ | 5.5 | 5.3 | 7.0 | 8.1 | 9.0 | 10.1 | 11.0 |
| TMP/DMH Ratio | 4.1 | 5.4 | 5.2 | 5.2 | 5.1 | 4.6 | 4.6 |
| Octanes |  |  |  |  |  |  |  |
| R + O | 95.8 | 96.8 | 97.1 | 95.6 | 96.1 | 96.2 | 95.5 |
| M + O | 93.0 | 94.3 | 93.8 | 93.8 | 94.2 | 93.0 | 92.9 |
| R + M/2 | 94.6 | 95.6 | 95.5 | 94.7 | 95.2 | 94.6 | 94.2 | operating constantly at 1000 rpm, and clearly shows the efficacy of separating alkylated product from the catalyst complex via decantation.

The receiver off-gas was passed through sodium hydroxide scrubbers to remove $BF_3$, and finally through a wet test meter. The total product composition was determined from gas chromatographic analyses of the liquid and off-gas samples.

Results are summarized in Table 1, and show that just prior to terminating $BF_3$ co-feed, the catalyst complex effected near 100% olefin conversion with a near-theoretical yield of 1.98 grams $C_5+$ per gram of $C_4$ olefin converted. See Example 1. Theoretical yield is 2.04 grams $C_5+$ per gram of $C_4$ olefin converted. The alkylate product was substantially paraffinic (as evidenced by bromine numbers less than 4) and contained roughly 86 weight % $C_8$ paraffins, 9.3 weight % $C_5$-$C_7$ paraffins, and 5.5 weight % $C_9+$ paraffins. The ratio of high octane trimethylpentanes to lower octane dimethylhexanes (TMP/DMH) was 4.1 and the corresponding octane was 94.6 (R+M)/2.

$BF_3$ co-feed was then discontinued. Surprisingly, when $BF_3$ cofeed was discontinued, excellent catalyst performance was still observed. See Examples 2-7. Such performance is clearly contrary to reasonable expectations, given that the catalytic efficacy of other liquid acidic catalyst systems such as hydrofluoric and sulfuric degrades rapidly in the absence of makeup acid or continuous regeneration and recycle of regenerated acid. Even more surprisingly, catalyst performance improved during the first several days of operation with no $BF_3$ addition. The presence of small amounts of $BF_3$ in the unit off-gas indicated that residual excess $BF_3$ was still present in the reaction zone. The TMP/DMH ratio increased to as high as 5.4 and the octane increased to over 95.5 (R+M)/2. Some gradual loss of activity/selectivity was observed over the next 5 days (olefin conversion dropped from 100% to 97%, the TMP/DMH ratio decreased from 5.4 to 4.6, the $C_9+$

TABLE 2

Effect of $BF_3$ Co-feed: $BF_3$ Phosphoric Acid Catalyst
(10/1 $IC_4$ =/2$C_4$ = Feed, 150 psig, 50° F.)

|  | Ex. 8 | Ex. 9 |
|---|---|---|
| $BF_3$ Cofeed (wt. % of Total Feed) | 0.5 | 8.7 |
| Time on Stream, hrs. | 151 | 161 |
| Olefin WHSV, $hr^{-1}$ | 0.4 | 0.3 |
| Product Distribution in $C_5+$, wt. % |  |  |
| $C_5$-$C_7$ | 10.9 | 16.5 |
| $C_8$'s | 82.9 | 74.2 |
| $C_9+$ | 6.2 | 9.3 |
| TMP/DMH Ratio | 4.0 | 2.3 |
| $C_5+$ Octane (R + M/2) | 94.7 | 89.8 |

Effect of $BF_3$ Co-feed: $BF_3:H_2O$ Catalyst
(10/1 $IC_4$ =/2$C_4$ = Feed, 150 psig, 50° F.)

|  | Ex. 10 | Ex. 11 | Ex. 12 |
|---|---|---|---|
| $BF_3$ Cofeed (wt. % of Total Feed) | 0.6 | 5.2 | 0.5 |
| Time on Stream, hrs. | 47 | 71 | 119 |
| Olefin WHSV, $hr^{-1}$ | 0.4 | 0.4 | 0.4 |
| Product Distribution in $C_5+$, wt. % |  |  |  |
| $C_5$-$C_7$ | 15.6 | 16.8 | 13.3 |
| $C_8$'s | 63.6 | 62.6 | 73.8 |
| $C_9+$ | 20.8 | 20.6 | 12.9 |
| TMP/DMH Ratio | 3.0 | 2.5 | 3.8 |
| $C_5+$ Octane (R + M/2) | 91.5 | 89.3 | 93.9 |

Changes and modifications in the specifically described embodiments can be carried out without departing from the scope of the invention which is intended to be limited only by the scope of the appended claims.

What is claimed is:

1. A continuous process for the alkylation of an isoparaffin with an olefin comprising the steps of:
   (a) contacting $H_3PO_4$ with sufficient $BF_3$ to evolve a catalyst complex containing from about 10 ppm (weight) to about 5.0 percent (weight) excess BF$_3$ based on the total isoparaffin and olefin feed;

(b) reacting an isoparaffin containing from 4 to 20 carbon atoms with an olefin containing from 2 to 12 carbon atoms in an alkylation reaction zone in the presence of said catalyst complex of step (a) under conversion conditions including temperature of from about $-40°$ C. to about 200° C. and pressure in the range of subatmospheric to about 5000 psig; and (c) withdrawing a product stream containing gasoline boiling range hydrocarbons and catalyst complex from said alkylation reaction zone of step (b) and recycling at least a portion of said catalyst complex to said alkylation reaction zone.

2. The process of claim 1 further comprising decanting said product stream of step (c) into a hydrocarbon phase and a catalyst complex phase.

3. The process of claim 1 further comprising deacidifying said hydrocarbon phase.

4. The process of claim 3 wherein said deacidification step comprises sorbing acidic components from said hydrocarbon phase.

5. The process of claim 3 further comprising contacting said hydrocarbon phase with a Lewis base.

6. The process of claim 5 wherein said Lewis base comprises at least one selected from the group consisting of Lewis bases which are normally solid under sorption conditions.

7. The process of claim 6 wherein said Lewis base comprises at least one selected from the group consisting of calcium fluoride (CaF$_2$), and polyvinyl alcohol (PVA).

8. The process of claim 5 wherein said Lewis base comprises at least one selected from the group consisting of Lewis bases which are normally liquid under sorption conditions.

9. The process of claim 8 wherein said Lewis base comprises at least one selected from the group consisting of diethylether, dioxane and anisole.

10. The process of claim 1 further comprising deacidifying said hydrocarbon phase by contacting said hydrocarbon phase with an aqueous alkaline solution.

11. The process of claim 10 wherein said aqueous alkaline solution comprises at least one selected from the group consisting of KOH and NaOH.

* * * * *

UNITED STATES PATENT AND TRADEMARK OFFICE
CERTIFICATE OF CORRECTION

PATENT NO. : 5,245,101
DATED : September 14, 1993
INVENTOR(S) : K. J. Del Rossi et al.

It is certified that error appears in the above-indentified patent and that said Letters Patent is hereby corrected as shown below:

On the title page, Item [73] Assignee: Mobil Oil Corporation, Fairfax, VA -- shoul be added Signed and Sealed this Twelfth Day of July, 1994

Attest:

BRUCE LEHMAN

*Attesting Officer*     *Commissioner of Patents and Trademarks*